United States Patent
Yushko et al.

(10) Patent No.: US 9,534,987 B2
(45) Date of Patent: Jan. 3, 2017

(54) APPARATUS, SYSTEM AND METHOD FOR REDUCING DEAD VOLUME IN A SAMPLE CONTAINER

(71) Applicant: Schlumberger Technology Corporation, Sugar Land, TX (US)

(72) Inventors: Maxim Yushko, Houston, TX (US); Ramon Hernandez Marti, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 685 days.

(21) Appl. No.: 13/865,867

(22) Filed: Apr. 18, 2013

(65) Prior Publication Data

US 2013/0276553 A1 Oct. 24, 2013

Related U.S. Application Data

(60) Provisional application No. 61/635,579, filed on Apr. 19, 2012.

(51) Int. Cl.
*G01N 1/20* (2006.01)
*E21B 49/08* (2006.01)

(52) U.S. Cl.
CPC ............ *G01N 1/20* (2013.01); *E21B 49/086* (2013.01); *G01N 1/2035* (2013.01); *G01N 2001/2071* (2013.01)

(58) Field of Classification Search
CPC G01N 1/20; G01N 1/2035; G01N 2001/2071; E21B 49/086
See application file for complete search history.

(56) References Cited

U.S. PATENT DOCUMENTS

| | | | |
|---|---|---|---|
| 3,705,610 A * | 12/1972 | Baudras | B67D 7/002 137/615 |
| 5,240,072 A | 8/1993 | Schultz et al. | |
| 5,337,822 A | 8/1994 | Massie et al. | |
| 6,467,544 B1 | 10/2002 | Brown et al. | |
| 6,820,636 B1 * | 11/2004 | Kien | F16L 55/134 137/15.15 |
| 6,964,301 B2 | 11/2005 | Hill et al. | |
| 7,367,394 B2 | 5/2008 | Villareal et al. | |
| 7,543,659 B2 | 6/2009 | Partouche et al. | |
| 7,546,885 B2 | 6/2009 | Longfield | |
| 7,594,541 B2 | 9/2009 | Ciglenec et al. | |
| 7,600,420 B2 | 10/2009 | Meek | |

(Continued)

OTHER PUBLICATIONS

International Search Report and the Written Opinion for International Application No. PCT/US2013/037277 dated Aug. 13, 2013.

*Primary Examiner* — Hezron E Williams
*Assistant Examiner* — David Z Huang
(74) *Attorney, Agent, or Firm* — Kenneth L. Kincaid

(57) ABSTRACT

An apparatus with a reduced dead volume associated with sampling, comprising: a sample container configured to store a fluid, a sample line configured to transport the fluid from a first sampling area to a second area in the sample container, at least one valve in the sample line, the valve configured to selectively range from a closed configuration to an open configuration, and a flow restrictor configuration placed in the sample line, the flow restrictor configured to minimize the dead volume for the sample container.

6 Claims, 4 Drawing Sheets

(56) References Cited

U.S. PATENT DOCUMENTS

| | | | |
|---|---|---|---|
| 8,167,002 B2* | 5/2012 | Kuhne | G05D 7/012 |
| | | | 137/504 |
| 2003/0070317 A1* | 4/2003 | Anderson | A23L 1/0151 |
| | | | 34/359 |
| 2007/0039757 A1* | 2/2007 | Nichols | E21B 7/28 |
| | | | 175/57 |
| 2011/0011583 A1* | 1/2011 | Niconoff | E21B 43/08 |
| | | | 166/264 |
| 2011/0024189 A1 | 2/2011 | Saeed et al. | |
| 2011/0113866 A1* | 5/2011 | Finlay | G01N 30/6095 |
| | | | 73/61.52 |
| 2011/0185809 A1* | 8/2011 | Guieze | G01N 1/2202 |
| | | | 73/32 R |
| 2011/0219786 A1* | 9/2011 | Andres | B64D 13/06 |
| | | | 62/7 |
| 2012/0074620 A1* | 3/2012 | Gillespie | F27D 3/1509 |
| | | | 266/45 |

\* cited by examiner

APPARATUS, SYSTEM AND METHOD FOR REDUCING DEAD VOLUME IN A SAMPLE CONTAINER

CROSS-REFERENCE TO RELATED APPLICATIONS

This disclosure claims priority to U.S. Provisional Application 61/635,759 filed Apr. 19, 2012, the entirety of which is incorporated by reference.

FIELD OF THE INVENTION

Aspects of the disclosure relate to containers. More specifically, aspects of the disclosure relate to containers used to store, test and transport fluids, especially in the oilfield industry.

BACKGROUND INFORMATION

Sample containers used to store, test and transport fluids are used in a number of industries. Generally, is typically advantageous to maintain the fluid at giving conditions, such as conditions as the fluid was at the time it was positioned in the sample container.

For example, in the oilfield industry, to sample and test fluids such as deposits of hydrocarbons and other desirable materials trapped in underground formations, a wellbore is drilled by connecting a drill bit to the lower end of a series of coupled sections of tubular pipe known as a drill string. A downhole sampling tool may be deployed in the wellbore drilled through the formations. The downhole sampling tool may include a fluid communication device, such as a probe or a straddle packer to establish fluid communication between the downhole sampling tool and a formation penetrated by the wellbore.

Fluid samples may be extracted from the formation via a fluid communication device using a fluid pump provided with the downhole sampling tool. Various downhole sampling tools for wireline and/or while-drilling applications are known in the art such as those described in U.S. Pat. Nos. 6,964,301, 7,594,541, 7,543,659 and 7,600,420, the entireties of which are incorporated herein.

Sampling tools may be provided with a plurality of sample bottles to receive and retain the fluid samples. Sample bottles include, for example, those described in U.S. Pat. Nos. 6,467,544, 7,367,394 and 7,546,885, the entireties of which are incorporated herein by reference.

SUMMARY

An apparatus with a reduced dead volume associated with sampling, comprising a sample container configured to store a fluid, a sample line configured to transport the fluid from a first sampling area to a second area in the sample container, at least one valve in the sample line, the valve configured to selectively range from a closed configuration to an open configuration, and a flow restrictor configuration placed in the sample line, the flow restrictor configured to minimize the dead volume for the sample container.

DETAILED DESCRIPTION

Figure 1A:
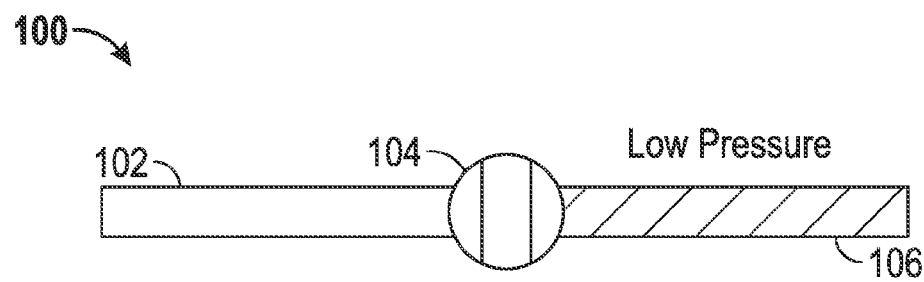
FIG. 1A is a side view of an insert used to occupy dead volume in a modular sample bottle formation tester at low pressure.
Figure 1B:
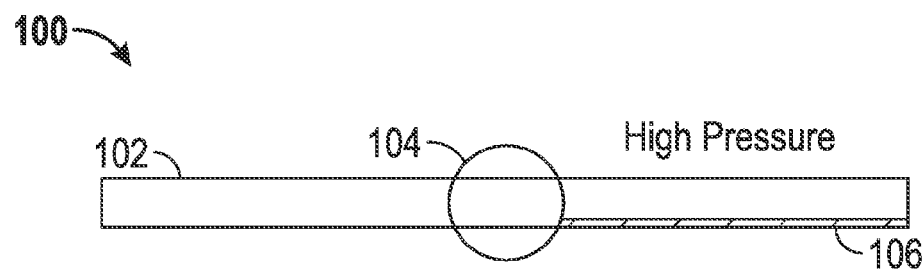
FIG. 1B is a side view of an insert used to occupy dead volume in a modular sample bottle formation tester at high pressure.

Referring to FIGS. 1A and 1B, one example embodiment of an arrangement for reducing the dead volume of a sample container 100 is illustrated. FIG. 1A depicts a first low pressure configuration for an arrangement disclosed. FIG. 1B depicts a second high pressure state of the arrangement disclosed in FIG. 1A. In the illustrated embodiment, the arrangement disclosed is used in a downhole sampling apparatus used in well services for the petroleum industry. Although the arrangement described is used in a downhole sampling apparatus, the arrangement may be used in other sampling environments, such as in a laboratory setting or other industrial sampling situations where accuracy is important and the potential for contamination or dilution of the fluid stream is possible.

A sample line 102 is configured to transport fluid from a source to the sample container 100. In the example embodiment, the fluid transported is a petroleum fluid and the source of the fluid is found in geological stratum in a downhole environment. The fluid may be, for example, black oil or condensates of natural gas, as non-limiting examples.

The fluid being sampled may be obtained through a probe placed in close proximity to the geological stratum where a pump module draws a vacuum, causing fluid to enter the probe and ultimately into the sample line 102. Additionally, the fluid being sampled may be obtained through a focused sampling packer. The sample line 102 may be insulated to keep the fluid in the same state, including pressure and temperature as much as possible to the sampling conditions.

The sample line 102 may connect to other sample lines throughout a string of tools, such as downhole tools or laboratory equipment so the sampled fluid may be provided to different configurations for appropriate testing. In sample containers, for example, a significant dead volume exists. This dead volume, in the form of a volume of material in sampling lines prior to the sampling container, may contain water and/or oil. When a sampled fluid enters the sample line 102 and enters the dead volume, the sampled fluid is mixed with the fluid contained in the dead volume. Contaminants may be introduced into the sampled fluid affecting overall testing results. Additionally, in the case of pure water being in the sample line, the pure water will dilute the sample fluid, again affecting overall results. Reduction of this sampled fluid mixing with dead volume fluid will increase the accuracy of results.

One alternative example embodiment used to reduce dead volume fluid in the sample line 102 is to use a flow restrictor 106 in the sample line 102. The flow restrictor 106 may be, for example, an expandable balloon. The flow restrictor, as illustrated in FIG. 1A, is fully inflated in times of relatively low pressure. The full inflation of the flow restrictor 106 prevents fluid from occupying through the dead volume area of the sample line 102, thereby minimizing the mixing of fluids between sampled fluids and fluids in the dead volume. Under times of higher pressure, as provided in FIG. 1B, the flow restrictor 106 is configured to deflate, thereby allowing fluid to flow along the sample line 102. This deflation allows sampling to occur during times of higher pressure, when a downhole tool is configured to be experiencing inflow. The deflation may be automatic after reaching a predefined pressure in the sample line 102 or may be done through actuation through an operator. In the illustrated embodiment, the deflation occurs automatically as the control equipment required for operator initiated deflation is deleted for clarity of illustration.

In another example embodiment, the flow restrictor 106 may be membrane material that is spring energized such that the spring force, per Hooke's law, is constant and that higher pressure values in the sample line 102 would cause additional deflection of the flow restrictor 106, causing a greater flow path area. In relatively low pressure environments, the spring steel strength causes the membrane to remain in contact with the walls of the sample line 102, therefore the dead volume is occupied and contamination is minimized. The flow restrictor 106 may be constructed from a high grade spring steel, for example, where the deflection capabilities are well known. In this embodiment, the membrane may be a fluid impervious material to prevent flow of fluids, thus the flow of fluids only occurs when deflection of the spring occurs.

In either embodiment, a valve 104 may be placed in the sample line 102. The valve 104 may be any kind of valve that would prevent fluid from flowing through the sample line 102. The valve 104 may be electronically activated to allow an operator the ability to select when fluid flow should occur through the sample line 102.

In another example embodiment, inert particles may be placed within the sample line 102 such that the inert particles occupy volume in the sample line 102. The inert particles may be kept in place by appropriate stops placed along the sample line. The inert particles may be placed in a container or membrane that allows fluid to flow through but retains particles within the container; or particles can be used without a container or membrane to allow particles follow the flow of fluid into the sample container 100 (to avoid plugging the flowline). The inert particles may be tightly packed or loosely packed or, in an alternative configuration, the inert particles may be graded such that amount of flow path area is restricted to an even greater amount. The particles may be placed in the line for several sampling (if contained by a membrane) operations or may be a single use arrangement (if not contained). The particles may be spherical, as a non-limiting embodiment.

Figure 2:
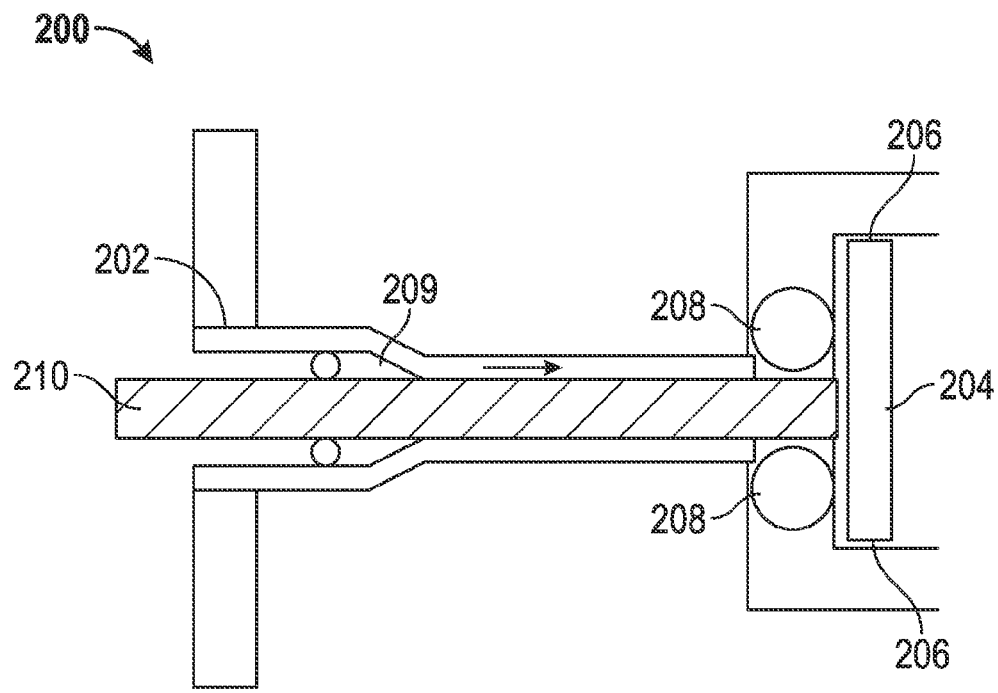
FIG. 2 is a side view of a sample bottle with an external plunger used to occupy dead volume in a modular sample bottle formation tester.

Referring to FIG. 2, an arrangement 200 for sampling fluids is illustrated. The arrangement 200 has an entry port 202 that allows fluid that is desired to be sampled into the arrangement 200. For the sake of clarity, the fluids, similar to the embodiment described in FIG. 2, are from a downhole environment, although the fluids may be obtained in other environments. The piston 204 in the sample bottle may be configured to move through piston seals 206 that contact the remainder of the bottle. The movement of the piston movement may allow for a vacuum to be drawn, thereby causing fluids to enter the bottle. In the illustrated embodiment, two bottle ball valves 208 are present. A plunger 210 may be used to occupy the dead space in the sample line between the entry port 202 and the bottle ball valve 208. This plunger 210 may be inserted or withdrawn, thereby occupying space or, in the case of withdrawal, allowing space. The plunger 210 may be activated by an operator, as desired. The plunger 210 may occupy all of the space between the entry port of the bottle ball valve or, in an alternative configuration, a portion of the dead volume between the entry port 202 and the bottle ball valve arrangement 208. The plunger 210 may be operable from a first fully inserted position to a second fully removed position. When fully inserted, the plunger 210 inside o-ring 208 blocks the fluid passage to the bottle. When the plunger is retracted, partially or all the way to restriction 209 if it occupies the full passage cross-section, fluid in the entry port 202 is allowed to come in contact with piston 204. A pump may then push the fluid into the sample chamber 200 displacing piston 204, or vacuum can be applied to the opposite side of piston 204, displacing it inside the sample chamber 200 forcing the fluid to be sampled into chamber 200. It can be appreciated that the plunger 210 takes most of the dead volume between entry port 202 and the face of the sampling bottle piston 204.

Figure 3:
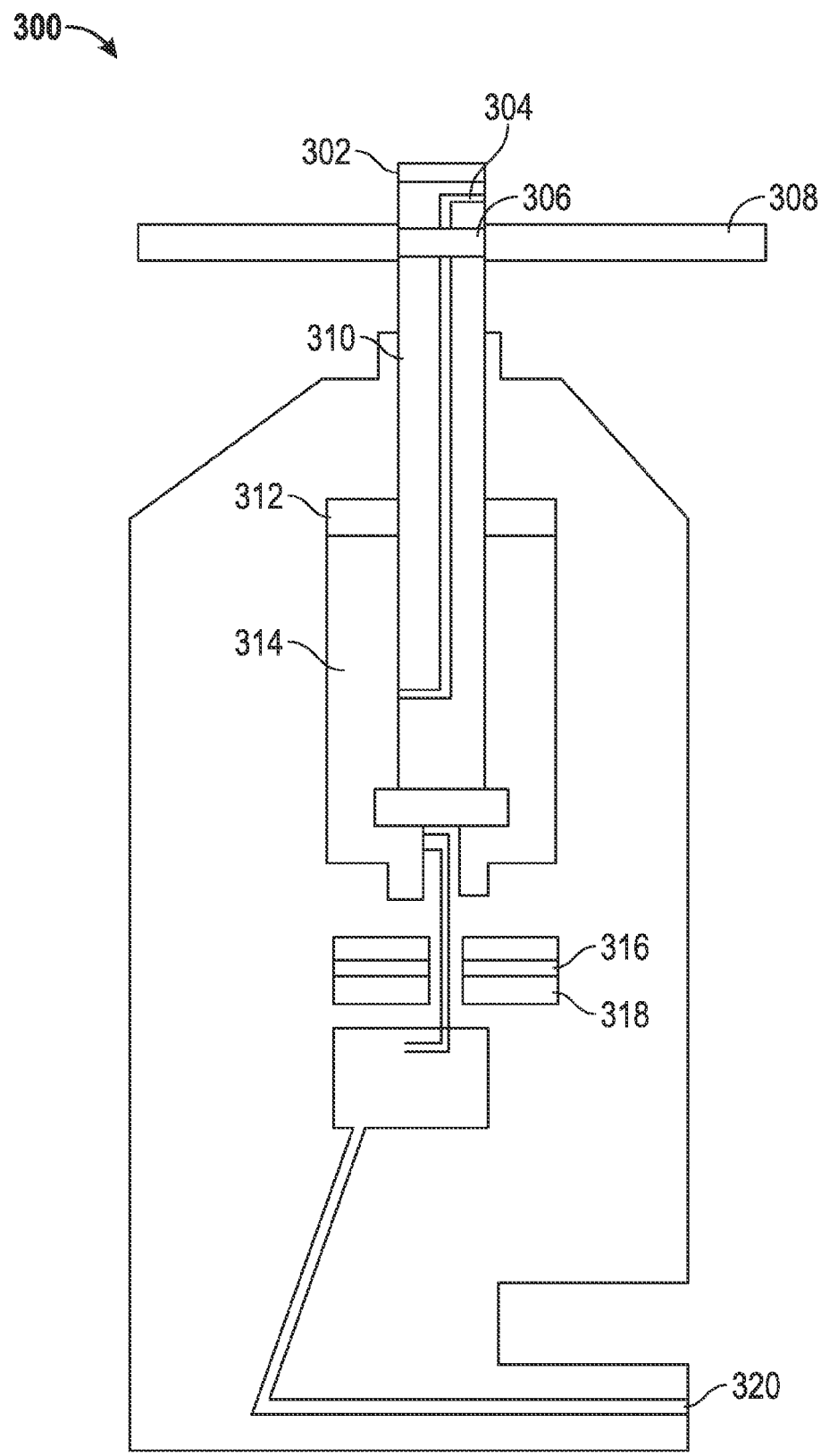
FIG. 3 is a side view of a sample bottle with an internal plunger used to occupy dead volume in a modular sample bottle formation tester.

Referring to FIG. 3, an arrangement 300 is disclosed for sampling fluids, wherein the arrangement 300 has a minimum of dead volume, maximizing accuracy of sampling. A top end of the piston rod 302 is configured with a blank end so that fluid may not pass through the top end 302 when it is aligned with the sample line 308. The piston rod 310 is further configured with a sample port 304 and a by-pass/flush line 306. The piston rod 310 is movable through a series of positions. In the fully retracted position, the top end 302 of the piston rod 310 is aligned with the sample line 308 preventing materials from entering the sample bottle and eventually sample chamber 314. The piston rod 310 is movable through a nitrogen piston 316 that is placed within a nitrogen chamber 318. Though action of the nitrogen piston 316, the piston rod 310 moves between the various series of positions where either the top end 302 of the piston, the sample port 304 or the by-pass/flush line 306 are aligned with the sample 308.

When the sample port 304 is aligned with the sample line 308 fluid may enter the piston rod 310 and pass down through to the sample chamber 314 for storage. Further activation of the piston rod 310 will cause the sample bottle to be closed, preventing fluid from escaping from the sample chamber 314. An admission control valve 320 is positioned at the opposite end of the top end 302 for allowing extraction of the fluid sample in the sample chamber 314.

Figure 4:
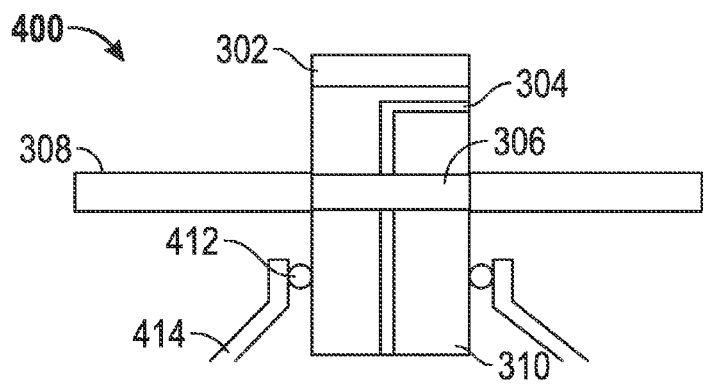
FIG. 4 is a side view of a sample bottle neck disposed in a sample carrier with a fully extended position of a piston rod.

Referring to FIG. 4, an expanded view of the piston rod end is illustrated. In the expanded view 400, the bypass-flush line 306 is aligned with the sample line 308 so that fluid passes through the piston rod 310 without entering the sample chamber 314.

Figure 5:
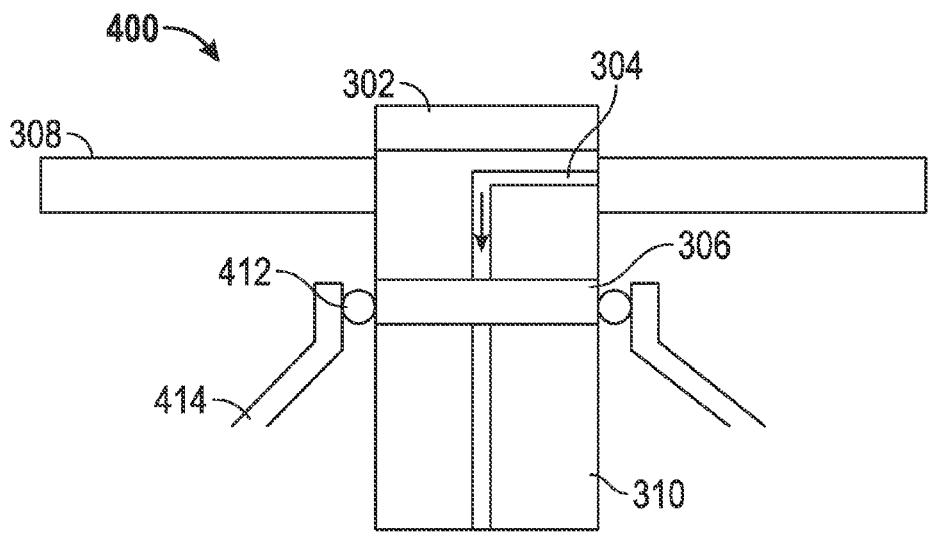
FIG. 5 is a side view of an extended piston rod and accompanying extension mechanism of an alternative embodiment of the modular sample bottle formation tester.

Referring to FIG. 5, an expanded view of the piston rod end is illustrated in a sampling configuration. In this position for the embodiment, the piston rod 310 position allows fluid to enter the sample port 304 which then travels down the piston rod 310 to the sample bottle 414. A seal 412 is provided on the sample bottle to allow the fluid to be retained in the sample bottle.

Figure 6:
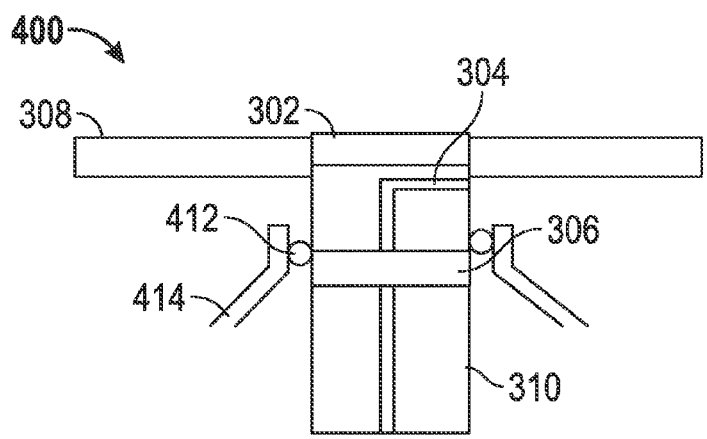
FIG. 6 is a side view of a sample chamber that is exposed to a flowline until the rod retracts and the seals trap a sample in the sample chamber.

Referring to FIG. 6, an expanded view of the piston rod end is illustrated in a sealed configuration. In this position for the embodiment, the piston rod 310 position is fully inserted into the bottle to trap fluid within the sample bottle 414.

Figure 7:
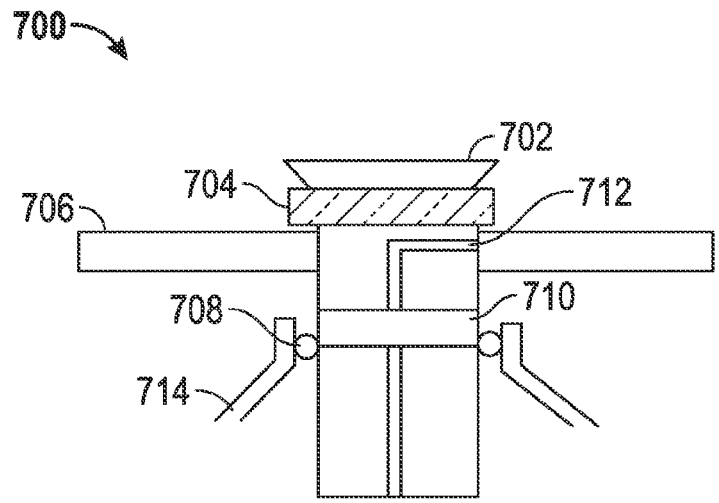
FIG. 7 is a side view of a sample chamber with associated EXO washers used for shifting rod positions for the modular sample bottle formation tester.

Referring to FIG. 7, an arrangement 700 is presented for limiting dead volume for a sample bottle 714. In the illustrated embodiment, a washer 704 prevents movement of the piston rod past a specific point. The washer 704 allows the sample port 712 to align with the sample line 706 so that fluid may enter the sample port 712 and be transferred down into the sample bottle 714. Fluid is kept in the sample bottle 714 through a sample bottle seal 708. The washer 704, although shown as a single washer, may be a series of washers to allow for step-wise insertion of the piston. The washer 704 may be selectively eliminated by an operator, so that a step progression of the piston occurs. Elimination may be accomplished by successive burning of the washers 704. Burning may occur through imposition of an electric charge on the washer. The control wiring to accomplish this electric charge is omitted for clarity of illustration. A flared end 702 prevents the piston from entering the bottle after elimination of the last washer 704. A bypass/flow line 710 is present in the piston to allow for flow to bypass the sample bottle 714 as necessary.

Figure 8:
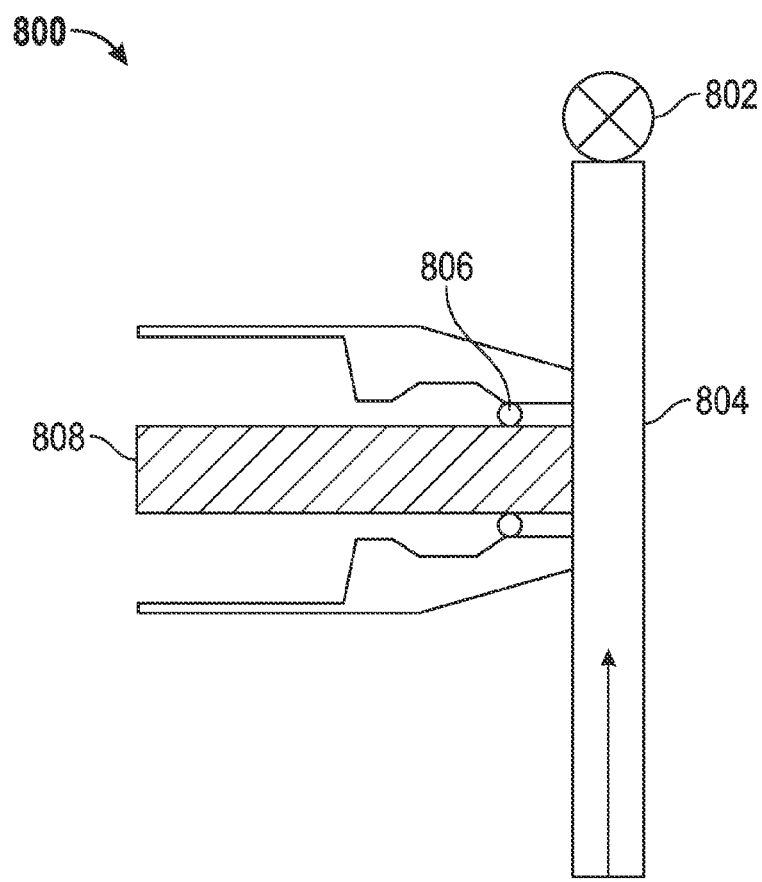
FIG. 8 is a side view of a sample chamber with a piston rod that is flush with the flowline of a modular sample bottle formation tester.

Referring to FIG. 8, a side view of a sample chamber with a piston rod 808 that is flush with the flowline 804 of a modular sample bottle formation tester 800. The piston rod 808 in the illustrated configuration is movable. The flow line 804 may have a valve 802 installed to limit or increase flow as desired. A gasket 806 or sealing device may abut the piston rod 808 to prevent flow from escaping or entering the back chamber. The valve 802 closing may cause a back pressure sufficient to allow movement of the piston rod 808 and consequently flow into the bottle. The process may be reversible such that the piston rod 808 may reciprocate back once the pressure diminishes. The piston rod 808 may be kept in place through spring actuation, as a non-limiting embodiment.

While the aspects has been described with respect to a limited number of embodiments, those skilled in the art, having benefit of this disclosure, will appreciate that other embodiments can be devised which do not depart from the scope of the disclosure herein.

What is claimed is:

1. An apparatus with a reduced dead volume associated with sampling, comprising:
   a sample container configured to store a fluid;
   a sample line configured to transport the fluid from a first sampling area to a second area in the sample container;
   at least one valve in the sample line, the at least one valve configured to selectively range from a closed configuration to an open configuration; and
   a flow restrictor configuration disposed within an interior volume of the sample line, the flow restrictor configured to reduce the dead volume for the sample container by the flow restrictor having a first configuration and a second configuration, wherein the flow restrictor occupies more of the interior volume of the sample line when in the second configuration than when in the first configuration, and wherein the flow restrictor comprises a piston rod with a sample port, the piston rod movable from an inserted closed position to a second fluid by-pass position to a third fluid sampling position, the piston rod having a channel in an internal of the rod extending from a first end of the rod to a second end of the rod and configured to transport fluid from the sample port near the first end of the rod to the sample container near the second end of the rod.

2. The apparatus according to claim 1, wherein the piston rod is further configured with a bypass-flush line disposed at the first end of the rod.

3. The apparatus according to claim 1, further comprising:
   a washer configured at an end of the piston rod with the sample port, where the washer is configured to maintain the piston rod at a specific point.

4. The apparatus according to claim 3, further comprising:
   an arrangement configured to selectively eliminate a plurality of washers by an operator via successive burning of the plurality of washers so the piston rod is not maintained at the specific point.

5. The apparatus according to claim 1, comprising:
   a nitrogen chamber; and
   a nitrogen piston in the nitrogen chamber movable from a first position to a second position, wherein movement of the piston moves the piston rod.

6. A method for sampling a fluid, comprising:
   positioning a sample container into a position to accept the fluid;
   sampling fluid through a sample port;
   transporting the fluid through a sample line, wherein the sample line has a flow restrictor disposed within an interior volume of the sample line;
   reducing the dead volume for the sample container by the flow restrictor having a first configuration and a second configuration, wherein the flow restrictor occupies more of the interior volume of the sample line when in the second configuration than when in the first configuration, and wherein the flow restrictor comprises a piston rod with a sample port, the piston rod movable from an inserted closed position to a second fluid by-pass position to a third fluid sampling position, the piston rod having a channel in an internal of the rod extending from a first end of the rod to a second end of the rod and configured to transport fluid from the sample port near the first end of the rod to the sample container near the second end of the rod; and
   accepting the sampling fluid in the sample container.

* * * * *